(12) United States Patent
Rittinghausen

(10) Patent No.: US 9,539,228 B2
(45) Date of Patent: Jan. 10, 2017

(54) COMPOSITION CONTAINING LYSINE AS A NUTRITIONAL SUPPLEMENT OR TREATMENT IN THE CASE OF HERPES

(71) Applicant: Reiner Rittinghausen, Inning-Bachern (DE)

(72) Inventor: Reiner Rittinghausen, Inning-Bachern (DE)

(73) Assignee: Reiner Rittinghausen, Inning-Bachern (DE)

( * ) Notice: Subject to any disclaimer, the term of this patent is extended or adjusted under 35 U.S.C. 154(b) by 0 days.

(21) Appl. No.: 14/430,878

(22) PCT Filed: Mar. 22, 2013

(86) PCT No.: PCT/EP2013/056145
§ 371 (c)(1),
(2) Date: Mar. 24, 2015

(87) PCT Pub. No.: WO2014/048584
PCT Pub. Date: Apr. 3, 2014

(65) Prior Publication Data
US 2015/0250752 A1    Sep. 10, 2015

(30) Foreign Application Priority Data
Sep. 28, 2012    (DE) .................... 20 2012 103 733 U

(51) Int. Cl.
| | | |
|---|---|---|
| *A61K 31/198* | (2006.01) | |
| *A61K 31/375* | (2006.01) | |
| *A61K 31/4415* | (2006.01) | |
| *A61K 31/519* | (2006.01) | |
| *A61K 31/714* | (2006.01) | |
| *A61K 33/00* | (2006.01) | |
| *A61K 45/06* | (2006.01) | |
| *A23L 1/302* | (2006.01) | |
| *A23L 1/304* | (2006.01) | |
| *A61K 31/525* | (2006.01) | |
| *A61K 33/30* | (2006.01) | |
| *A61K 9/00* | (2006.01) | |
| *A61K 9/68* | (2006.01) | |

(52) U.S. Cl.
CPC ............ *A61K 31/198* (2013.01); *A23L 33/105* (2016.08); *A23L 33/15* (2016.08); *A23L 33/16* (2016.08); *A23L 33/175* (2016.08); *A61K 9/0056* (2013.01); *A61K 9/0058* (2013.01); *A61K 31/375* (2013.01); *A61K 31/4415* (2013.01); *A61K 31/519* (2013.01); *A61K 31/525* (2013.01); *A61K 31/714* (2013.01); *A61K 33/30* (2013.01); *A61K 45/06* (2013.01); *A23V 2002/00* (2013.01)

(58) Field of Classification Search
CPC   A61K 2300/00; A61K 31/198; A61K 31/375; A61K 31/4415; A61K 31/519; A61K 31/525; A61K 31/714; A61K 33/30; A61K 45/06; A61K 9/0056; A61K 9/0058; A23L 1/3002; A23L 1/302; A23L 1/304
See application file for complete search history.

(56) References Cited

U.S. PATENT DOCUMENTS

| | | | |
|---|---|---|---|
| 6,362,225 B1 | 3/2002 | Andreakos | |
| 6,455,061 B2 | 9/2002 | Richardson | |
| 7,025,996 B1 * | 4/2006 | Miladinov | ............... A23L 1/296 424/725 |
| 2007/0134320 A1 * | 6/2007 | Lowder | ................ A61K 31/195 424/464 |

FOREIGN PATENT DOCUMENTS

| | | |
|---|---|---|
| DE | 102 21 403 | 12/2003 |
| DE | 202008016372 | 4/2009 |
| EP | 1064946 | 1/2001 |
| WO | WO 03/035027 | 5/2003 |

OTHER PUBLICATIONS

Spallholz et al. (Nutrition: chemistry and biology;1998, 2nd Ed. CRC Press: p. 41).*
Consumer Lab RDA [online] retrieved on Mar. 8, 2016 from:https://www.consumerlab.com/RDAs/; 5 pages.*
English translation of DE10221403 Dec. 4, 2002; 10 pages.*
Flodin, N.W. "The metabolic roles, pharmacology, and toxicology of lysine", Journal of the American College of Nutrition, American College of Nutrition Wilmington, NC, US. Feb. 1, 1997. vol. 16, No. 1, 7-21.
Barkhoff, Frauke. "Hilfe bei Herpesinfektionen und Gürtelrose" Neue Wege Zur Gesundheit, Constantia Verlag. Jul. 7, 2001. vol. 15, No. 7.
International Search Report Issued in corresponding International Application PCT/EP2013/056145. Dated Aug. 1, 2013.
Austrian Search Report Issued in corresponding International Application PCT/EP2013/056145. Dated Jan. 30, 2015.
English translation of the international preliminary report on patentability in corresponding International application No. PCT/EP2013/056145 dated Apr. 17, 2015.

* cited by examiner

*Primary Examiner* — Ernst V Arnold
(74) *Attorney, Agent, or Firm* — Davidson, Davidson & Kappel, LLC

(57) ABSTRACT

The invention relates to a composition comprising, related to a daily dose of the composition, as its active ingredients L-lysine ranging from ≥750 mg to −9 g, suitable as a nutritional supplement or prophylactic and/or therapeutic treatment in cases of herpes infections and/or inflammations of the oral and pharyngeal zones, particularly in acute therapy.

19 Claims, No Drawings

COMPOSITION CONTAINING LYSINE AS A NUTRITIONAL SUPPLEMENT OR TREATMENT IN THE CASE OF HERPES

This application is a U.S. national phase application under 35 U.S.C. §371 of International Application No. PCT/EP2013/056145, filed Mar. 22, 2013, which claims priority to German Application No. DE 20 2012103733.5, filed Sep. 28, 2012, the disclosures of which is hereby incorporated by reference herein.

BACKGROUND OF THE INVENTION

Herpes is an infectious disease caused by viruses. There are many different herpes viruses. The herpes viruses pathogenic to humans include the Herpes simplex viruses herpes virus type 1 (HSV-1) and herpes virus type 2 (HSV-2) which causes in particular genital herpes (Herpes genitalis). The herpes viruses pathogenic to humans furthermore include the varicella zoster virus which causes chickenpox or shingles (Herpes zoster), the Epstein-Barr virus which causes glandular fever, the cytomegalovirus which causes infection of the salivary gland and the human herpes virus type 6 (HHV-6) which causes three-day fever.

The Herpes simplex virus type 1 (HSV-1) in particular is widely encountered. It is estimated that about 90% of the population of Central Europe is infected with herpes virus type 1. In most cases, the primary infection occurs during the first years in someone's life. This infection is frequently latent; however, some children come down with herpetic gingivostomatitis (Gingivostomatitis herpetica). Since the viruses remain latent in the body, about 15% to 30% of those infected repeatedly suffer from eruptions of cold sores (Herpes labialis) in the later years of life. Triggers can be a cold and fever, physical exhaustion, stress, hormonal imbalances, sun or heat exposure and also feelings of disgust.

Currently, there are no known active compounds capable of killing herpes viruses in the body or capable of removing the viruses from the body. Customary methods for the treatment of cold sores comprise the application of lip creams comprising chemical active compounds which are supposed to inhibit the replication of the virus (virustatics), for example aciclovir. Creams or gels comprising zinc sulfate, which also has antiviral action, are likewise known. However, topical administration of zinc solutions may cause painful or irritating side-effects.

In the literature, there are furthermore references concerning the administration of vitamin C, zinc or the amino acid L-lysine as a preventative measure or when the first symptoms appear. Here, vitamin C acts by enhancing the defenses, whereas zinc stimulates the immune system. Since the herpes virus requires the amino acid L-arginine for replication, arginine-rich food should be avoided if possible, whereas more lysine-rich food should be consumed by virtue of its ability to inhibit arginine uptake. Although a lysine-rich and arginine-poor diet may represent a prophylactic measure to prevent a herpes outbreak, this is not suitable as a treatment. There is therefore a need for a composition which can provide an effective treatment for cold sores.

SUMMARY OF THE INVENTION

Accordingly, it is an object of the present invention to provide a composition which overcomes at least one of the above-mentioned disadvantages of the prior art. In particular, it is an object of the present invention to provide a composition which can be used for the treatment of herpes infections.

The object is achieved by a composition comprising, based on a daily dose of the composition, as active component L-lysine in the range from $\geq 750$ mg to $\geq 9$ g.

In a further embodiment, the object is achieved by a composition suitable in particular as a nutritional supplement or prophylactic and/or therapeutic treatment for herpes infections and/or inflammations of the oral cavity and the throat, wherein the composition comprises, based on a daily dose of the composition, as active ingredients the substances below:

L-lysine in the range from $\geq 750$ mg to $\leq 9$ g, and
zinc in the range from $\geq 9$ mg to $\leq 90$ mg, and is present in an administration form selected from the group comprising chewable tablets, chewable coated pills, lozenges, pastilles, orally disintegrating tablets, gels, metered dose sprays and/or chewing gums.

Surprisingly, it has been found that the composition according to the invention can reduce the duration of a herpes infection. This is a great advantage since a herpes infection, from the outbreak beginning with itching, tingling or a sensation of pain on the lips until the scabs have healed, generally lasts for about two weeks. In addition, cold sores are painful and a great strain for those affected, also for esthetic reasons. Shortening the duration of the infection for several or even just one day is thus a primary feature of a treatment. Surprisingly, it has furthermore been found that administration of L-lysine and zinc using the range of amounts according to the invention may reduce the infectiousness of herpes viruses.

Furthermore, the composition according to the invention may suppress the development of blisters in the case of beginning itching or sensation of pain on the lips. In addition, using the composition according to the invention it may also be possible to achieve prophylaxis of herpes infections and/or inflammations of the oral cavity and the throat before symptoms occur. Thus, for example, when there are indications of herpes-triggering factors such as a cold or a feeling of disgust, administration of the composition may prevent the outbreak and/or the frequency of herpes infections.

In an advantageous manner, the compositions according to the invention may display a good effect in the nutritional, prophylactic and/or therapeutic treatment of herpes infections and/or inflammations of the oral cavity and the throat. Furthermore, it was found that it was also possible to notice an improvement as adjunct therapy with other herpes therapeutics.

The present invention accordingly furthermore relates to a composition comprising, based on a daily dose of the composition, as active component L-lysine in the range from $\geq 750$ mg to $\leq 9$ g for use as a nutritional supplement or prophylactic and/or therapeutic treatment of herpes infections and/or inflammations of the oral cavity and the throat, in particular of cold sores.

Yet further, the present invention accordingly relates to a composition comprising, based on a daily dose of the composition, as active ingredients the substances below:

L-lysine in the range from $\geq 750$ mg to $\leq 9$ g, and
zinc in the range from $\geq 9$ mg to $\leq 90$ mg, and present in an administration form selected from the group comprising chewable tablets, chewable coated pills, lozenges, pastilles, orally disintegrating tablets, gels, metered dose sprays and/or chewing gums, for use as a nutritional supplement or prophylactic and/or therapeutic treatment of herpes infections and/or inflammations of the oral cavity and the throat, in particular of cold sores.

A particular advantage is the rapid onset of action. The outbreak of a herpes infection makes itself felt by itching or a sensation of pain on the lips, prior to blisters being formed. Surprisingly, it has been found that, when the composition was taken as soon as symptoms occurred, it was possible to suppress the outbreak of a herpes infection. Here, it is particularly advantageous that there was an instant onset of action and that the patients were virtually symptom-free even on the next day. This permits in particular administration of the composition in an acute treatment as a single and/or repeat temporary administration which does not have to be initiated prior to the occurrence of a herpes infection and does not have to be administered for a relatively long time to achieve an effect.

Accordingly, the present invention furthermore relates to a composition comprising, based on a daily dose of the composition, as active component L-lysine in the range from ≥750 mg to ≤9 g, for use in the acute treatment of herpes infections and/or inflammations of the oral cavity and the throat, in particular the acute treatment of cold sores. It is a very particular advantage that even just lysine may have good efficacy in the acute treatment of herpes infections, in particular cold sores.

Yet further, the present invention relates to a composition comprising, based on a daily dose of the composition, as active ingredients the substances below:

L-lysine in the range from ≥750 mg to ≤9 g, and
zinc in the range from ≥9 mg to ≤90 mg, and present in an administration form selected from the group comprising chewable tablets, chewable coated pills, lozenges, pastilles, orally disintegrating tablets, gels, metered dose sprays and/or chewing gums, for use in the acute treatment of herpes infections and/or inflammations of the oral cavity and the throat, in particular the acute treatment of cold sores.

For the purpose of the present invention, the term "acute treatment" is to be understood as meaning an administration which achieves, at the time of or after occurrence of a disease, an advantageous effect, without this requiring prior long-term administration, i.e. for several days, weeks or months independent of disease states. Thus, during an "acute treatment" for the purpose of the present invention, there is alleviation of the complaints without any prophylactic administration and/or a long-term or continuous treatment independent of disease states being required. In particular, for the purpose of the present invention, the term "acute treatment" comprises that the composition according to the invention can, when a herpes infection is noticed, have a rapid effect, for example within a day, or prevent an outbreak including the formation of blisters.

Preference is given to an administration form selected from the group comprising chewable tablets, chewable coated pills, lozenges, pastilles, orally disintegrating tablets, gels, metered dose sprays and/or chewing gums. It is assumed that the positive effect of the composition is based in particular on the administration form selected from the group comprising chewable tablets, chewable coated pills, lozenges, pastilles, orally disintegrating tablets, gels, metered dose sprays and/or chewing gums. Thus, these administration forms, in particular a chewable tablet, may provide instant improved bioadsorption through the oral mucosa. Thus, following administration a chewable tablet quickly dissolves in the mouth. Moreover, this provides an effect directly in the region of the mouth, wherein the cold sores occur. Chewing in particular spreads the active compounds over a wide area in the region of the mouth. This furthermore provides an advantage as compared to administration via tablets, capsules or drinking ampoules which are swallowed without chewing. The administration forms according to the invention are chewed, sucked or allowed to disintegrate in the mouth, with the active compounds being released as early as in the oral cavity. By the chewing process, these are thereby provided in metered form and by the chewing process initially substantially uniformly bioabsorbable.

In addition, administration of tablets requires water or other beverages. This is complicated, whereas transportation and use of administration forms such as chewable tablets, chewable coated pills, lozenges, pastilles, orally disintegrating tablets, gels, metered dose sprays or chewing gums is simple and convenient.

By administration of active compounds via a chewable tablet, chewable coated pill, lozenge, pastille, orally disintegrating tablet, gel, metered dose spray or a chewing gum, it is furthermore possible to administer the active compounds to the body over a certain administration time. During this time, there can be bioabsorption both via the oral mucosa and via the digestive tract if the active compounds are swallowed with the saliva and get into the stomach. This allows effective administration of the active compounds to be achieved via the mucosa of mouth and throat and also via the digestive tract. In this manner, through the systemic uptake, an effect on other herpes infections is possible in addition to an effect on cold sores or inflammations of the oral cavity and the throat.

The administration forms according to the invention are chewable or, in the case of the lozenges, pastilles and orally disintegrating tablets, suckable. A gel can remain in the mouth for longer than a liquid, and spread therein. Gels are semisolid preparations for use in the oral cavity. Metered dose sprays are similar. The pharmacopoeia does not list chewable tablets as a distinct administration form; however, they differ from lozenges by their weight, which is usually higher and can be in the range from 1.5 g to 3 g, for example, and by a longer disintegration time. Chewable coated pills are coated with a film. Orally disintegrating tablets are uncoated tablets which are kept in the mouth where they spread rapidly before they are swallowed. Lozenges and pastilles are solid single-dose preparations intended for sucking to obtain a usually localized effect in the oral cavity and in the throat. They dissolve slowly or disintegrate on sucking. Active compound-containing chewing gums are solid single-dose preparations having a base material consisting mainly of rubber. They are intended for chewing, but not for swallowing. The active compounds are released on chewing. Customary and physiologically acceptable basic materials and auxiliaries for preparing the administration forms are known to the person skilled in the art.

For the purpose of the present invention, the term "daily dose" is to be understood as meaning the amount of the composition which is administered per day, wherein the amount of substance administered per day should be within the stated ranges for the amounts of the substances in question. The term daily dose may be understood as meaning the amount ingested per day.

For the purpose of the present invention, the term "substance" is to be understood as meaning the substances present in the composition, in particular selected from the group comprising zinc, lysine, selenium, vitamin $B_2$, vitamin $B_6$, vitamin $B_{12}$, vitamin C, vitamin $D_3$, folic acid and/or bioflavonoids.

Data in mg or µg referring to zinc and also to selenium in each case refer to the metal, but these metals may be present, for example, in the form of inorganic and/or organic salts. Zinc is preferably present in the form of inorganic and/or organic salts. Preferred inorganic salts are selected from the group comprising zinc chloride, zinc oxide, zinc sulfate and/or zinc hydroxide. Preferred organic salts are selected from the group comprising zinc acetate, zinc aspartate, zinc gluconate, zinc orotate and/or zinc lactate.

The human body processes amino acids in their L form. Accordingly, for the purpose of the present invention, the term "lysine" is used synonymously to "L-lysine". L-Lysine is an endogenous amino acid.

It is advantageous that the amounts of lysine and zinc present according to the invention cannot result in an overdosage. In preferred embodiments, the composition comprises, based on a daily dose of the composition, as active ingredients:

L-lysine in the range from ≥1.5 g to ≤6 g, with preference 3 g, and zinc in the range from ≥15 mg to ≤60 mg, with preference 30 mg.

These daily dosages are particularly effective in suppressing a herpes outbreak or in shortening the duration of the infection. In the context of a prophylaxis of herpes infections and/or inflammations of the oral cavity and the throat, these daily doses are likewise effective in suppressing a herpes outbreak.

The composition is suitable for use as a food supplement or for the prophylactic and/or therapeutic dietary treatment of herpes infections and/or inflammations of the oral cavity and the throat.

For the purpose of the present invention, the term "herpes infections" is to be understood as meaning infections caused by herpes viruses pathogenic to humans such as the Herpes simplex viruses, the varicella zoster virus, the Epstein-Barr virus, the cytomegalovirus and the human herpes virus type 6. Herpes infections are preferably selected from the group comprising cold sores (Herpes labialis), herpetic gingivostomatitis (Gingivostomatitis herpetica), genital herpes (Herpes genitalis), chickenpox or shingles (Herpes zoster), glandular fever, infection of the salivary gland and/or three-day fever. Preferred herpes infections are infections caused by Herpes simplex, in particular herpes virus type 1, viruses, in particular cold sores (herpes labialis) and herpetic gingivostomatitis (gingivostomatitis herpetica).

Herpetic gingivostomatitis or gingivostomatitis herpetica, also referred to as aphthous stomatitis, stomatitis aphthosa or stomatitis herpetica, is a disease of the oral mucosa and the gums caused by the herpes virus Herpes simplex type 1 (HSV-1).

For the purpose of the present invention, the term "inflammations of the oral cavity and the throat" is to be understood as meaning inflammations affecting the oral cavity and the throat including the gums and the mucosa of the throat. Inflammations of the oral cavity and the throat are in particular viral inflammations; however, they can also comprise inflammations caused by bacteria.

Preferred are inflammations of the oral cavity and the throat selected from the group comprising gingivitis, stomatitis and/or pharyngitis. The term "gingivitis" is to be understood as meaning inflammations of the marginal gums (gingiva). Gum inflammations are in most cases caused by bacteria; however, they can also be caused by viruses. The term "stomatitis" is to be understood as meaning inflammations of the oral mucosa. Inflammations of the oral mucosa can be caused infectiously by viruses. The term "pharyngitis" or "inflammation of the throat" is to be understood as meaning inflammations of the mucosa of the throat. Pharyngitis can be caused by influenza- or adenoviruses, but also by Herpes simplex viruses. The Epstein-Ban virus and the cytomegalovirus may also cause an inflammation of the throat.

The composition may comprise further active ingredients. In some embodiments, the composition may comprise active ingredients selected from the group comprising selenium, vitamin $B_2$, vitamin $B_6$, vitamin $B_{12}$, vitamin C, vitamin $D_3$, folic acid and/or bioflavonoids. A combination with selenium, vitamin $B_2$, vitamin $B_6$, vitamin $B_{12}$, vitamin C, vitamin $D_3$, folic acid and bioflavonoids may be particularly advantageous for the purpose of the invention. These may provide an improved protection against herpes infections and/or inflammations of the oral cavity and the throat. A combination with selenium, vitamin $B_2$, vitamin $B_6$, vitamin $B_{12}$, vitamin C, vitamin $D_3$, folic acid and/or bioflavonoids may contribute in particular in generally supporting an intact antiviral defense mechanism.

For the purpose of the present invention, the term "bioflanovoids" is to be understood as meaning natural flavonoids obtainable from plants. They can be obtained, for example, from the skin of citrus fruits. For the purpose of the present invention, the term "citrus bioflavonoids" is to be understood as meaning natural flavonoids obtained from the skin of citrus fruits. The bioflavonoids include, for example, hesperidin, rutin and quercitin. Selenium is preferably present in the form of selenite, selenate and/or selenium yeast. Vitamin C may be present in natural and/or synthetic form. "Natural vitamin C" is to be understood as meaning vitamin C in "food-bound" form, for example as citrus concentrate. Vitamin C may furthermore be present in the form of isolated ascorbic acid or isolated mineral ascorbate which, in most cases, is prepared synthetically.

In preferred embodiments, the composition may comprise, based on a daily dose of the composition, as active ingredients:

selenium in the range from ≥10 µg to ≤300 µg, with preference in the range from ≥50 µg to ≤200 µg, preferably 100 µg; and/or vitamin $B_2$ in the range from ≥1.8 mg to ≤100 mg, with preference in the range from ≥4.5 mg to ≤50 mg, preferably 6 mg; and/or vitamin $B_6$ in the range from ≥1.8 mg to ≤100 mg, with preference in the range from ≥4.5 mg to ≤50 mg, preferably 6 mg; and/or vitamin $B_{12}$ in the range from ≥1 µg to ≤100 µg, with preference in the range from ≥2 µg to ≤30 µg, preferably 6 µg; and/or vitamin C in the range from ≥25 mg to ≤2 g, with preference in the range from ≥50 mg to ≤1 g, preferably 500 mg; and/or vitamin $D_3$ in the range from ≥1 µg to ≤50 µg, with preference in the range from ≥2.5 µg to ≤20 µg, preferably 5 µg; and/or folic acid in the range from ≥50 µg to ≤2 mg, with preference in the range from ≥100 µg to ≤1 mg, preferably 500 µg; and/or bioflanovoids in the range from ≥1 mg to ≤100 mg, with preference in the range from ≥2.5 mg to ≤50 mg, preferably 5 mg.

In particular, it is advantageous that the dosages of the composition according to the invention do not cause any side-effects. This allows the composition to be used not only with beginning itching, sensation of pain or formation of blisters on the lips, but also even when there are indications of herpes-triggering factors such as a cold, sun exposure, stress or feelings of disgust.

In some embodiments, the composition according to the invention comprises, per 100 g of composition, 21 g of L-lysine, 213 mg of zinc, 709 mg of selenium, 43 mg of vitamin B2, 43 mg of vitamin B6, 43 mg of vitamin B12, 3547 mg of vitamin C, 35 mg of vitamin D3, 3547 mg of folic acid and 36 mg of citrus bioflavonoids.

The composition is preferably present in the form of a solid or a gel. From among the administration forms selected from the group comprising chewable tablet, chewable coated pill, lozenge, pastille, orally disintegrating tablet, gel, metered dose spray and/or chewing gum, preference is given to chewable tablets, chewable coated pills and lozenges, in particular chewable tablets. A chewable tablet in particular may provide instant improved bioadsorption through the oral mucosa. Thus, following administration a chewable tablet quickly dissolves in the mouth. Moreover, this provides an effect directly in the region of the mouth, where the cold sores occur. Chewing of a chewable tablet in particular spreads the active compounds over a wide area in the region of the mouth. In addition, by the chewing process, these are provided in metered form and in a substantially uniformly bioabsorbable manner. Chewable tablets have the further advantage that they can be chewed very easily without water. In preferred embodiments, the composition is therefore present in the form of a chewable tablet.

An administration form may comprise the substances and/or the contents by weight of substance in the amount of a daily dose. Furthermore, it may be intended that the daily dose can be administered divided into one or more single doses, for example two, three, four, five or six single doses. The daily dose and/or single dose may also be divided into a plurality of identical or different preparation forms, where the preparation forms may comprise identical or different substances and/or contents by weight of substance.

A particular advantage of the administration of the substances present as a plurality of separate doses is a longer overall duration of action in the region of the mouth. The daily dose of the composition may be present in the form of 1 to 6 single doses, with preference 2 to 5 single doses, in particular 3 or 4 single doses. The daily dose of the composition may be present in particular in the form of 1 to 6, with preference 2 to 5, in particular 3 or 4 chewable tablets, chewable coated pills, lozenges, pastilles, orally disintegrating tablets, gel or metered dose spray portions and/or chewing gums. Preferably, a daily dose is present in the form of 3 chewable tablets. Also preferably, a daily dose is present in the form of four chewable tablets.

For the purpose of the present application, the term "single dose" is to be understood as meaning a dosage unit of the composition. A single dose corresponds, for example, to one chewable tablet, one chewable coated pill, one lozenge, one pastille, one orally disintegrating tablet, one portion of gel or spray or one chewing gum.

In preferred embodiments, the composition comprises, based on a single dose of the composition, as active ingredients:

L-lysine in the range from ≥250 mg to ≤3 g, with preference in the range from ≥500 mg to ≤2 g, preferably 1 g, and
zinc in the range from ≥3 mg to ≤30 mg, with preference in the range from ≥5 mg to ≤20 mg, preferably 10 mg.

In more preferred embodiments, the composition, based on a single dose of the composition, may comprise as active ingredients:

selenium in the range from ≥3.3 µg to ≤100 µg, with preference in the range from ≥16.7 µg to ≤66.7 µg, preferably 33.3 µg; and/or
vitamin $B_2$ in the range from ≥0.6 mg to ≤33.3 mg, with preference in the range from ≥1.5 mg to ≤16.7 mg, preferably 2 mg; and/or
vitamin $B_6$ in the range from ≥0.6 mg to ≤33.3 mg, with preference in the range from ≥1.5 mg to ≤16.7 mg, preferably 2 mg; and/or
vitamin $B_{12}$ in the range from ≥0.3 µg to ≤33.3 µg, with preference in the range from ≥0.7 µg to ≤10 µg, preferably 2 µg; and/or
vitamin C in the range from ≥8.3 mg to ≤666.7 mg, with preference in the range from ≥16.7 mg to ≤333.3 mg, preferably 166.7 mg; and/or
vitamin $D_3$ in the range from ≥0.3 µg to ≤16.7 µg, with preference in the range from ≥0.8 µg to ≤6.7 µg, preferably 1.7 µg; and/or
folic acid in the range from ≥16.7 µg to ≤666.7 µg, with preference in the range from ≥33.3 µg to ≤333.3 µg, preferably 166.7 µg; and/or
bioflanovoids in the range from ≥0.3 mg to ≤33.3 mg, with preference in the range from ≥0.8 mg to ≤16.7 mg, preferably 1.7 mg.

The composition can be a functional food, dietary food, a supplementary balanced diet and/or a food supplement. With particular preference, the composition is a dietary food for special medical purposes, in particular for a balanced diet.

Accordingly, a further subject matter relates to food, in particular functional food, dietary food, compositions for a supplementary balanced diet and/or food supplements, comprising as active ingredients the substances of the composition, in particular, based on a daily dose of the foods, L-lysine in the range from ≥750 mg to ≤9 g, and zinc in the range from ≥9 mg to ≤90 mg, wherein the food is present in an administration form selected from the group comprising chewable tablets, chewable coated pills, lozenges, pastilles, orally disintegrating tablets, gels, metered dose sprays and/or chewing gums. Optionally, the food may furthermore comprise selenium, vitamin $B_2$, vitamin $B_6$, vitamin $B_{12}$, vitamin C, vitamin $D_3$, folic acid and/or bioflavonoids.

By virtue of the advantageous substances of the composition, the latter can be used in particular in the context of a dietary nutrition counseling, as food supplement or as a composition for a supplementary balanced diet. The composition is suitable in particular for use as a composition for a supplementary balanced diet and/or as a food supplement composition for the prophylaxis and/or treatment of herpes infections and/or inflammations of the oral cavity and the throat.

Preference is given to using the composition according to the invention for preparing a functional food, a dietary food, a supplementary balanced diet and/or food supplement, in particular as a nutritional supplement or prophylactic and/or therapeutic treatment of herpes infections, in particular of cold sores (Herpes labialis) or herpetic gingivostomatitis (Gingivostomatitis herpetica) and/or inflammations of the oral cavity and the throat, in particular selected from the group comprising gingivitis, stomatitis and/or pharyngitis.

Particular preference is given to the use for the acute treatment of herpes infections and/or inflammations of the oral cavity and the throat, in particular for the acute treatment of cold sores.

Herpes infections are preferably selected from the group comprising cold sores (Herpes labialis), herpetic gingivostomatitis (Gingivostomatitis herpetica), genital herpes (Herpes genitalis), chickenpox or shingles (Herpes zoster), glandular fever, infection of the salivary gland and/or three-day fever. Preferred herpes infections are infections caused by Herpes simplex viruses, in particular by herpes virus type 1, in particular cold sores (Herpes labialis) and herpetic gingivostomatitis (Gingivostomatitis herpetica).

Preferred inflammations of the oral cavity and the throat are selected from the group comprising gingivitis, stomatitis and/or pharyngitis.

The composition according to the invention is particularly suitable as a nutritional supplement or prophylactic and/or therapeutic dietary treatment for herpes infections and/or inflammations of the oral cavity and the throat.

DETAILED DESCRIPTION OF THE INVENTION

Examples of compositions, which serve to illustrate the present invention, are given below.

It goes without saying that the administration forms selected from the group comprising chewable tablets, chewable coated pills, lozenges, pastilles, orally disintegrating tablets, gels, metered dose sprays and/or chewing gums comprise the customary auxiliaries used for formulating the administration forms, so that the examples only list the active compounds present.

Example 1

A chewable tablet comprising 1 g of L-lysine and 10 mg of zinc.

Example 2

A chewable tablet comprising the following substances:
1 g of L-lysine
10 mg of zinc
33.3 µg of selenium
2 mg of vitamin $B_2$
2 mg of vitamin $B_6$
2 µg of vitamin $B_{12}$
166.7 mg of vitamin C
1.7 µg of vitamin $D_3$
166.7 µg of folic acid
1.7 mg of bioflavonoids.

Example 3

Composition comprising 3 chewable tablets comprising a total of the following substances:
3 g of L-lysine
30 mg of zinc.

Example 4

Composition comprising 3 chewable tablets comprising a total of the following substances:
3 g of L-lysine
30 mg of zinc
100 µg of selenium
6 mg of vitamin $B_2$
6 mg of vitamin $B_6$
6 µg of vitamin $B_{12}$
500 mg of vitamin C
5 µg of vitamin $D_3$
500 µg of folic acid
5 mg of bioflavonoids.

Example 5

A chewable coated pill comprising 1 g of L-lysine and 10 mg of zinc.

Example 6

A lozenge comprising 1 g of L-lysine and 10 mg of zinc.

Example 7

A chewing gum comprising 1 g of L-lysine and 10 mg of zinc.

Example 8

A sachet comprising a portion of gel comprising 1 g of L-lysine and 10 mg of zinc.

Example 9

The effect of the composition according to the invention described in Example 4 and comprising 3 chewable tablets was observed in patients with recurring cold sore infections. Here, when there were symptoms of itching, tingling or a sensation of pain on the lips, a chewable tablet was administered three times per day for two to five days.

It was found that by administering the composition according to the invention described in Example 4, it was possible to achieve a marked reduction of the frequency of cold sore eruption even after two to three days. Even on repeated and/or long-term administration, no contraindications or side-effects were observed; in particular, there were no intolerances.

Example 10

The effect of the composition according to the invention was observed in an application study comprising 64 participants suffering from recurring cold sore infections, where the study participants suffered from cold sores at least once to six times or more per year. Here, 31 participants took only the chewable tablet, whereas 33 participants took the chewable tablet as adjunct therapy in addition to further medicaments such as aciclovir or zinc cream, lip patches or immunostimulants for the treatment of herpes.

Participants of the study received chewable tablets comprising 1 g of L-lysine, 10 mg of zinc, 33.3 µg of selenium, 2 mg of vitamin $B_2$, 2 mg of vitamin $B_6$, 2 µg of vitamin $B_{12}$, 166.7 mg of vitamin C, 1.7 µg of vitamin $D_3$, 166.7 µg of folic acid and 1.7 mg of bioflavonoids. When there were symptoms of itching, tingling or a sensation of pain on the lips, the participants took in each case three chewable tablets per day, the administration being carried out over five days.

For the participants who took only the chewable tablet, a noticeable improvement of the symptoms was observed after on average 2.5 days, whereas conventional state-of-the-art therapies showed an improvement only after 4.8 days. Participants who took the chewable tablet as adjunct therapy showed a noticeable improvement of the symptoms after 4.2 days on average, as compared to 4.8 days.

Some participants who took only the chewable tablet when there was a beginning itching or sensation of pain on the lips did not notice any outbreak of the herpes infection by formation of blisters. Another fraction of the participants who took only the chewable tablet noticed that they were virtually symptomless even on the next day. This shows that, if the composition is taken early enough, it is possible to suppress an outbreak of the herpes infection. In particular, this shows that, if the composition according to the invention is administered in the sense of an acute treatment, it is possible to obtain an effect. Furthermore, in the case of 17 of the participants who took only the chewable tablet and 11 of the participants who took the chewable tablet as adjunct therapy for treating herpes, the herpes had healed completely on day 5 at the latest. In contrast, with conventional therapies only four participants were free of symptoms on day 5.

In particular, not only the efficacy but also the smell of the chewable tablets was found to be very good.

This shows that, by using the composition according to the invention, it is possible to reduce rapidly the symptoms of a herpes infection, and that the composition according to the invention is suitable in particular for an acute therapy. Furthermore, it was found that an improvement was also noticed when the composition was administered as adjunct therapy with other herpes therapeutics.

The invention claimed is:

1. A composition suitable for prophylactic and/or therapeutic treatment for herpes infections and/or inflammations of the oral cavity and the throat, characterized in that the composition comprises, based on a daily dose of the composition, as active ingredients the substances below:
   L-lysine in the range from ≥750 mg to ≤9 g,
   zinc in the range from ≥9 mg to ≤90 mg,
   selenium,
   vitamin B2,
   vitamin B6,
   vitamin B12,
   vitamin C,
   vitamin D3,
   folic acid and
   bioflavonoids
   and is present in an administration form selected from the group comprising chewable tablets, chewable coated pills, lozenges, pastilles, orally disintegrating tablets, gels, and/or chewing gums, which are chewed, sucked or allowed to disintegrate in the mouth, with the active ingredients being released in the oral cavity to provide an effect directly in the region of the mouth, wherein the composition comprises an effective amount of the active ingredients to treat herpes infections and/or inflammation of the oral cavity and throat.

2. The composition as claimed in claim 1, characterized in that the composition comprises, based on a daily dose of the composition, as active ingredients:
   L-lysine in the range from ≥1.5 g to ≤6 g, and
   zinc in the range from ≥15 mg to ≤60 mg.

3. The composition as claimed in claim 1, characterized in that the composition, based on a daily dose of the composition, comprises as active ingredients:
   selenium in the range from ≥10 μg to ≤300 μg; and/or
   vitamin $B_2$ in the range from ≥1.8 mg to ≤100 mg; and/or
   vitamin $B_6$ in the range from ≥1.8 mg to ≤100 mg; and/or
   vitamin $B_{12}$ in the range from ≥1 μg to ≤100 μg; and/or
   vitamin C in the range from ≥25 mg to ≤2 g; and/or
   vitamin $D_3$ in the range from ≥1 μg to ≤50 μg; and/or
   folic acid in the range from ≥50 μg to ≤2 mg; and/or
   bioflavonoids in the range from ≥1 mg to ≤100 mg.

4. The composition as claimed in claim 1, characterized in that the composition is present in the form of a chewable tablet.

5. The composition as claimed in claim 1, characterized in that the composition, based on a single dose of the composition, comprises as active ingredients:
   L-lysine in the range from ≥250 mg to ≤3 g, and
   zinc in the range from ≥3 mg to ≤30 mg, preferably 10 mg.

6. The composition as claimed in claim 1, based on a single dose of the composition, comprises as active ingredients:
   selenium in the range from ≥3.3 μg to ≤100 μg; and/or
   vitamin $B_2$ in the range from ≥0.6 mg to ≤33.3 mg; and/or
   vitamin $B_6$ in the range from ≥0.6 mg to ≤33.3 mg; and/or
   vitamin $B_{12}$ in the range from ≥0.3 μg to ≤33.3 μg; and/or
   vitamin C in the range from ≥8.3 mg to ≤666.7 mg; and/or
   vitamin $D_3$ in the range from ≥0.3 μg to ≤16.7 μg; and/or
   folic acid in the range from ≥16.7 μg to ≤666.7 μg; and/or
   bioflavonoids in the range from ≥0.3 mg to ≤33.3 mg.

7. The composition of claim 2, wherein the composition comprises, based on a daily dose of the composition, as active ingredients:
   3 g L-lysine, and
   30 mg zinc.

8. The composition of claim 3, wherein the composition comprises, based on a daily dose of the composition, as active ingredients:
   selenium in the range from ≥50 μg to ≤200 μg; and/or
   vitamin $B_2$ in the range from ≥4.5 mg to ≤50 mg; and/or
   vitamin $B_6$ in the range from ≥4.5 mg to ≤50 mg; and/or
   vitamin $B_{12}$ in the range from ≥2 μg to ≤30 μg; and/or
   vitamin C in the range from ≥50 mg to ≤1 g; and/or
   vitamin $D_3$ in the range from ≥2.5 μg to ≤20 μg; and/or
   folic acid in the range from ≥100 μg to ≤1 mg; and/or
   bioflavonoids in the range from ≥2.5 mg to ≤50 mg.

9. The composition of claim 3, wherein the composition comprises, based on a daily dose of the composition, as active ingredients:
   100 μg selenium;
   6 mg vitamin $B_2$;
   6 mg vitamin $B_6$;
   6 μg vitamin $B_{12}$;
   500 mg vitamin C;
   5 μg vitamin $D_3$;
   500 μg folic acid; and
   5 mg bioflavonoids.

10. The composition of claim 5, wherein the composition comprises, based on a single dose of the composition, as active ingredients:
    L-lysine in the range from ≥500 mg to ≤2 g, and
    zinc in the range from ≥5 mg to ≤20 mg.

11. The composition of claim 5, wherein the composition comprises, based on a single dose of the composition, as active ingredients:
    1 g L-lysine, and
    10 mg zinc.

12. The composition of claim 6, wherein the composition comprises, based on a single dose of the composition, as active ingredients:
    selenium in the range from ≥16.7 μg to ≤66.7 μg; and/or
    vitamin $B_2$ in the range from ≥1.5 mg to ≤16.7 mg; and/or
    vitamin $B_6$ in the range from ≥1.5 mg to ≤16.7 mg; and/or
    vitamin $B_{12}$ ce in the range from ≥0.7 μg to ≤10 μg; and/or
    vitamin C in the range from ≥16.7 mg to ≤333.3 mg; and/or
    vitamin $D_3$ in the range from ≥0.8 μg to ≤6.7 μg; and/or
    folic acid in the range from ≥33.3 μg to ≤333.3 μg; and/or
    bioflavonoids in the range from ≥0.8 mg to ≤16.7 mg.

13. The composition of claim 6, wherein the composition comprises, based on a single dose of the composition, as active ingredients:

33.3 µg selenium;
2 mg vitamin $B_2$;
2 mg vitamin $B_6$;
2 µg vitamin $B_{12}$;
166.7 mg vitamin C;
1.7 µg vitamin $D_3$;
166.7 µg folic acid; and
1.7 mg bioflavonoids.

14. A composition suitable for prophylactic and/or therapeutic treatment for herpes infections and/or inflammations of the oral cavity and the throat, characterized in that the composition consists essentially of, based on a daily dose of the composition, as active ingredients the substances below:
L-lysine in the range from ≥750 mg to ≤9 g,
zinc in the range from ≥9 mg to ≤90 mg,
selenium,
vitamin B2,
vitamin B6,
vitamin B12,
vitamin C,
vitamin D3,
folic acid and
bioflavonoids
and is present in an administration form selected from the group comprising chewable tablets, chewable coated pills, lozenges, pastilles, orally disintegrating tablets, gels, and/or chewing gums, which are chewed, sucked or allowed to disintegrate in the mouth, with the active ingredients being released in the oral cavity to provide an effect directly in the region of the mouth, wherein the composition comprises an effective amount of the active ingredients to treat herpes infections and/or inflammation of the oral cavity and throat.

15. A method of treating herpes infections and/or inflammations of the oral cavity and the throat, the method comprising the step of administering the composition of claim 1.

16. The method of claim 15, wherein the herpes infection is selected from cold sores and herpetic gingivostomatitis.

17. The method of claim 15, wherein the inflammations of the oral cavity and the throat are selected from the group comprising gingivitis, stomatitis and/or pharyngitis.

18. The method of claim 15, wherein the treatment is an acute treatment of herpes infections and/or inflammations of the oral cavity and the throat.

19. The method of claim 15, wherein the treatment is the acute treatment of cold sores.

* * * * *